US008774930B2

(12) United States Patent
Ball

(10) Patent No.: US 8,774,930 B2
(45) Date of Patent: Jul. 8, 2014

(54) ELECTROMAGNETIC BONE CONDUCTION HEARING DEVICE

(75) Inventor: Geoffrey R. Ball, Axams (AT)

(73) Assignee: Vibrant Med-El Hearing Technology GmbH, Innsbruck (AT)

( * ) Notice: Subject to any disclaimer, the term of this patent is extended or adjusted under 35 U.S.C. 154(b) by 0 days.

(21) Appl. No.: 13/604,759

(22) Filed: Sep. 6, 2012

(65) Prior Publication Data

US 2013/0035540 A1 Feb. 7, 2013

Related U.S. Application Data

(60) Continuation-in-part of application No. 13/163,965, filed on Jun. 20, 2011, now abandoned, and a continuation-in-part of application No. 13/462,931, filed on May 3, 2012, which is a division of application No. 12/839,887, filed on Jul. 20, 2010, now abandoned.

(60) Provisional application No. 61/356,717, filed on Jun. 21, 2010, provisional application No. 61/227,632, filed on Jul. 22, 2009.

(51) Int. Cl.
*A61N 1/40* (2006.01)
*A61N 1/36* (2006.01)

(52) U.S. Cl.
CPC .................................. *A61N 1/36032* (2013.01)
USPC ................... 607/57; 607/55; 607/56; 600/25; 381/312

(58) Field of Classification Search
CPC ............. A61N 1/0541; A61N 1/36032; H04R 25/606; H04R 2460/13; H04R 2225/021
USPC .......................... 607/55–57; 600/25; 381/312
See application file for complete search history.

(56) References Cited

U.S. PATENT DOCUMENTS

| | | | | |
|---|---|---|---|---|
| 3,487,403 | A | 12/1969 | Pihl | 340/373 |
| 3,573,812 | A | 4/1971 | Pihl | 340/373 |

(Continued)

FOREIGN PATENT DOCUMENTS

| | | | |
|---|---|---|---|
| EP | 2031896 | 4/2009 | H04R 25/00 |
| GB | 1468890 | 3/1977 | |

(Continued)

OTHER PUBLICATIONS

Bromberg & Sunstein LLP, Response A filed May 14, 2007 to Office Action dated Feb. 12, 2007, pertaining to U.S. Appl. No. 11/158,322, 11 pages.

(Continued)

*Primary Examiner* — Michael Kahelin
*Assistant Examiner* — Christopher A Flory
(74) *Attorney, Agent, or Firm* — Sunstein Kann Murphy & Timbers

(57) ABSTRACT

An external component for a hearing implant is described. An external housing contains an attachment magnet configured to magnetically connect with an implant magnet of an implanted signal transducer. A pair of external electromagnetic drive coils within the external housing are adjacent to the attachment magnet for conducting electrical current to develop magnetic drive signals through the skin to the signal transducer to generate responsive vibrations of the signal transducer for perception by the patient as sound. The drive coils are configured such that their respective magnetic drive signals have opposing magnetic directions.

5 Claims, 5 Drawing Sheets

(56) References Cited

U.S. PATENT DOCUMENTS

| | | | | |
|---|---|---|---|---|
| 3,801,767 | A | 4/1974 | Marks | 200/161 |
| 3,987,967 | A | 10/1976 | Kuznetsov et al. | 241/1 |
| 4,038,990 | A | 8/1977 | Thompson | 128/419 PG |
| 4,199,741 | A | 4/1980 | Serrus Paulet | 335/206 |
| 4,257,936 | A | 3/1981 | Matsumoto et al. | 524/413 |
| 4,317,969 | A | 3/1982 | Riegler et al. | 200/52 R |
| 4,549,532 | A * | 10/1985 | Baermann | 600/15 |
| 4,596,971 | A | 6/1986 | Hirabayashi et al. | 335/205 |
| 4,628,907 | A * | 12/1986 | Epley | 600/25 |
| 4,785,816 | A | 11/1988 | Dow et al. | 128/660 |
| RE32,947 | E | 6/1989 | Dormer et al. | 128/420.6 |
| 4,868,530 | A | 9/1989 | Ahs | 335/207 |
| 4,918,745 | A | 4/1990 | Hutchison | 455/41 |
| 4,936,305 | A * | 6/1990 | Ashtiani et al. | 607/57 |
| 5,015,224 | A * | 5/1991 | Maniglia | 600/25 |
| 5,183,056 | A | 2/1993 | Dalen et al. | 128/782 |
| 5,430,801 | A * | 7/1995 | Hill | 381/322 |
| 5,434,549 | A | 7/1995 | Hirabayashi et al. | 335/229 |
| 5,456,654 | A | 10/1995 | Ball | 600/25 |
| 5,522,865 | A * | 6/1996 | Schulman et al. | 607/56 |
| 5,538,219 | A | 7/1996 | Osterbrink | 251/129.15 |
| 5,554,096 | A | 9/1996 | Ball | 600/25 |
| 5,624,376 | A * | 4/1997 | Ball et al. | 600/25 |
| 5,630,835 | A | 5/1997 | Brownlee | 607/60 |
| 5,716,407 | A | 2/1998 | Knapp et al. | 623/11 |
| 5,724,014 | A | 3/1998 | Leikus et al. | 335/4 |
| 5,749,912 | A | 5/1998 | Zhang et al. | 607/57 |
| 5,772,575 | A * | 6/1998 | Lesinski et al. | 600/25 |
| 5,800,336 | A * | 9/1998 | Ball et al. | 600/25 |
| 5,824,022 | A * | 10/1998 | Zilberman et al. | 607/57 |
| 5,857,958 | A | 1/1999 | Ball et al. | 600/25 |
| 5,877,664 | A | 3/1999 | Jackson, Jr. | 335/205 |
| 5,897,486 | A | 4/1999 | Ball et al. | 600/25 |
| 5,913,815 | A * | 6/1999 | Ball et al. | 600/25 |
| 6,040,762 | A | 3/2000 | Tompkins | 340/426 |
| 6,067,474 | A | 5/2000 | Schulman et al. | 607/57 |
| 6,175,767 | B1 | 1/2001 | Doyle, Sr. | 607/57 |
| 6,178,079 | B1 | 1/2001 | Renger | 361/118 |
| 6,178,353 | B1 * | 1/2001 | Griffith et al. | 607/61 |
| 6,190,305 | B1 * | 2/2001 | Ball et al. | 600/25 |
| 6,208,235 | B1 | 3/2001 | Trontelj | 340/10.1 |
| 6,208,882 | B1 | 3/2001 | Lenarz et al. | 600/379 |
| 6,217,508 | B1 * | 4/2001 | Ball et al. | 600/25 |
| 6,219,580 | B1 | 4/2001 | Faltys et al. | 607/57 |
| 6,277,148 | B1 * | 8/2001 | Dormer | 623/10 |
| 6,292,678 | B1 | 9/2001 | Hall et al. | 600/374 |
| 6,295,472 | B1 | 9/2001 | Rubinstein et al. | 607/55 |
| 6,313,551 | B1 | 11/2001 | Hazelton | 310/12 |
| 6,348,070 | B1 * | 2/2002 | Teissl et al. | 623/11.11 |
| 6,358,281 | B1 * | 3/2002 | Berrang et al. | 623/10 |
| 6,475,134 | B1 | 11/2002 | Ball et al. | 600/25 |
| 6,505,062 | B1 | 1/2003 | Ritter et al. | 600/407 |
| 6,506,987 | B1 | 1/2003 | Woods | 290/61.62 |
| 6,522,909 | B1 | 2/2003 | Garibaldi et al. | 600/424 |
| 6,838,963 | B2 | 1/2005 | Zimmerling et al. | 335/205 |
| 7,091,806 | B2 | 8/2006 | Zimmerling et al. | 335/207 |
| 7,190,247 | B2 | 3/2007 | Zimmerling | 335/205 |
| 7,266,209 | B1 * | 9/2007 | House | 381/331 |
| 7,338,035 | B2 | 3/2008 | Tsai | 267/136 |
| 7,566,296 | B2 | 7/2009 | Zimmerling et al. | 600/25 |
| 7,608,035 | B2 | 10/2009 | Farone | 600/9 |
| 7,642,887 | B2 * | 1/2010 | Zimmerling | 335/296 |
| 8,241,201 | B2 * | 8/2012 | Hakansson | 600/25 |
| 8,246,532 | B2 * | 8/2012 | Ball et al. | 600/25 |
| 8,280,522 | B2 * | 10/2012 | Zierhofer et al. | 607/61 |
| 2001/0031996 | A1 * | 10/2001 | Leysieffer | 607/57 |
| 2004/0012470 | A1 * | 1/2004 | Zimmerling et al. | 335/207 |
| 2005/0004629 | A1 * | 1/2005 | Gibson et al. | 607/60 |
| 2005/0048646 | A1 * | 3/2005 | Nieda et al. | 435/372 |
| 2005/0062567 | A1 | 3/2005 | Zimmerling et al. | 335/150 |
| 2006/0244560 | A1 * | 11/2006 | Zimmerling et al. | 335/207 |
| 2007/0191673 | A1 | 8/2007 | Ball et al. | 600/25 |
| 2007/0274551 | A1 | 11/2007 | Tsai et al. | 381/326 |
| 2007/0282156 | A1 * | 12/2007 | Konings | 600/13 |
| 2008/0103350 | A1 * | 5/2008 | Farone | 600/13 |
| 2008/0123866 | A1 * | 5/2008 | Rule et al. | 381/71.6 |
| 2009/0209806 | A1 | 8/2009 | Hakansson | 600/25 |
| 2010/0004716 | A1 | 1/2010 | Zimmerling et al. | 607/57 |
| 2010/0145135 | A1 | 6/2010 | Ball et al. | 600/25 |
| 2010/0324355 | A1 | 12/2010 | Spitaels et al. | 600/25 |
| 2011/0022120 | A1 * | 1/2011 | Ball et al. | 607/57 |
| 2011/0216927 | A1 | 9/2011 | Ball | 381/313 |
| 2012/0029267 | A1 * | 2/2012 | Ball | 600/25 |
| 2012/0238799 | A1 * | 9/2012 | Ball et al. | 600/25 |

FOREIGN PATENT DOCUMENTS

| | | | | |
|---|---|---|---|---|
| JP | 04/023821 | | 1/2004 | H04R 25/00 |
| SU | 1690749 | | 11/1991 | A61F 11/04 |
| WO | WO 97/32629 | | 9/1997 | A61N 1/32 |
| WO | WO 00/10361 | | 2/2000 | |
| WO | WO 03/036560 | A2 | 5/2003 | G06K 11/18 |
| WO | WO 03/081976 | A2 | 10/2003 | |
| WO | WO 03/092326 | A1 | 11/2003 | H04R 25/00 |
| WO | WO 2004/114723 | | 12/2004 | H04R 25/00 |

OTHER PUBLICATIONS

Bromberg & Sunstein LLP, Response B filed Jun. 17, 2008 to Office Action dated Mar. 17, 2008, pertaining to U.S. Appl. No. 11/158,322, 10 pages.

Bromberg & Sunstein LLP, Response C filed Sep. 19, 2008 to Office Action dated Jun. 26, 2008, pertaining to U.S. Appl. No. 11/671,132, 8 pages.

Bromberg & Sunstein LLP, Response D filed Jan. 5, 2009 to Office Action dated Oct. 27, 2008, pertaining to U.S. Appl. No. 11/671,132, 13 pages.

European Patent Office, European Search Report (Extended) pertaining to Application No. 08075886.5-2205/12031896, date of mailing Jun. 3, 2009, 8 pages.

Heller et al, "Evaluation of MRI Compatibility of the Modified Nucleus Multichannel Auditory Brainstem and Cochlear Implants", *The American J. of Otology* 17(5); pp. 724-729 (Sep. 1996).

Hobbs, et al, "Magnetic Resonance Image—Guided Proteomics of Human Glioblastoma Multiforme", *Journal of Magnetic Resonance Imaging*; pp. 530-536 (2003).

International Searching Authority, International Search Report International Application No. PCT/IB03/02283, date of mailing Nov. 28, 2003, 4 pages.

International Searching Authority, Invitation to Pay Additional Fees—International Application No. PCT/IB2004/002588, date of mailing Dec. 20, 2004, 4 pages.

Teissl et al, "Cochlear Implants: In Vitro Investigation of Electromagnetic Interference at MR Imaging—Compatibility and Safety Aspects", *Radiology* 208(3); pp. 700-708 (Sep. 1998).

Teissl et al, "Magnetic Resonance Imaging and Cochlear Implants: Compatibility and Safety Aspects", *J Magn. Reson. Imaging* 9(1); pp. 26-38 (Jan. 1999).

United States Patent and Trademark Office, Office Action dated Feb. 12, 2007, pertaining to U.S. Appl. No. 11/158,322, 6 pages.

United States Patent and Trademark Office, Office Action dated Mar. 17, 2008, pertaining to U.S. Appl. No. 11/158,322, 14 pages.

United States Patent and Trademark Office, Office Action dated Oct. 27, 2008, pertaining to U.S. Appl. No. 11/671,132, 7 pages.

International Searching Authority, Authorized Officer Lee W. Young, International Search Report and Written Opinion, PCT/US11/41045, mailed Oct. 25, 2011, 10 pages.

International Searching Authority, Authorized Officer Shane Thomas, International Search Report and Written Opinion, PCT/US12/70823, date of mailing Mar. 13, 2013, 13 pages.

* cited by examiner

ELECTROMAGNETIC BONE CONDUCTION HEARING DEVICE

This application is a continuation in part of U.S. patent application Ser. No. 13/163,965, filed Jun. 20, 2011, which in turn claims priority from U.S. Provisional Patent 61/356,717, filed Jun. 21, 2010; and is a continuation in part of U.S. patent application Ser. No. 13/462,931, filed May 3, 2012, which is a divisional of U.S. patent application Ser. No. 12/839,887, filed Jul. 20, 2010, which in turn claims priority from U.S. Provisional Patent 61/227,632, filed Jul. 22, 2009; all of which are incorporated herein by reference.

FIELD OF THE INVENTION

The present invention relates to medical implants, and more specifically to a novel transcutaneous auditory prosthetic implant system.

BACKGROUND ART

A normal ear transmits sounds as shown in FIG. 1 through the outer ear 101 to the tympanic membrane (eardrum) 102, which moves the ossicles of the middle ear 103 (malleus, incus, and stapes) that vibrate the oval window 106 and round window 107 membranes of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the cochlear nerve 105 reside. In response to received sounds transmitted by the middle ear 103, the fluid-filled cochlea 104 functions as a transducer to generate electric pulses which are transmitted to the cochlear nerve 105, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid or middle ear implant may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

Middle ear implants employ electromagnetic transducers to convert sounds into mechanical vibration of the middle ear 103. A coil winding is held stationary by attachment to a non-vibrating structure within the middle ear 103 and microphone signal current is delivered to the coil winding to generate an electromagnetic field. A magnet is attached to an ossicle within the middle ear 103 so that the magnetic field of the magnet interacts with the magnetic field of the coil. The magnet vibrates in response to the interaction of the magnetic fields, causing vibration of the bones of the middle ear 103. See U.S. Pat. No. 6,190,305, which is incorporated herein by reference.

U.S. Patent Publication 20070191673 (incorporated herein by reference) describes another type of implantable hearing prosthesis system which uses bone conduction to deliver an audio signal to the cochlea for sound perception in persons with conductive or mixed conductive/sensorineural hearing loss. An implanted floating mass transducer (FMT) is affixed to the temporal bone. In response to an externally generated electrical audio signal, the FMT couples a mechanical stimulation signal to the temporal bone for delivery by bone conduction to the cochlea for perception as a sound signal. A certain amount of electronic circuitry must also be implanted with the FMT to provide power to the implanted device and at least some signal processing which is needed for converting the external electrical signal into the mechanical stimulation signal and mechanically driving the FMT.

SUMMARY OF THE INVENTION

Embodiments of the present invention include an external component for an implantable hearing prosthesis of a recipient patient. An external housing contains an attachment magnet configured to magnetically connect with an implant magnet of an implanted signal transducer. A pair of external electromagnetic drive coils within the external housing are adjacent to the attachment magnet for conducting electrical current to develop magnetic drive signals through the skin to the signal transducer to generate responsive vibrations of the signal transducer for perception by the patient as sound. The drive coils are configured such that their respective magnetic drive signals have opposing magnetic directions.

There also may be a signal processor for generating electrical drive signals for the electromagnetic drive coils. The signal processor may be enclosed within the external housing, or within a signal processor housing separate from and connected to the external housing. There also may be at least one sensing microphone for developing an audio input signal to the signal processor.

DETAILED DESCRIPTION OF SPECIFIC EMBODIMENTS

Various embodiments of the present invention are directed to an implantable hearing prosthesis for a recipient patient. An implant component and an external signal drive component each have two main lobes characterized by a distinctive magnet arrangement and a flexible connector member that maintains a constant distance between the two main lobes. One of the external main lobes contains a sensing microphone, an audio signal processor, and an attachment magnet which magnetically connects with a corresponding implant attachment magnet that forms one of the implant main lobes. The other external main lobe contains a ring drive magnet surrounding an electromagnetic signal drive coil that generates a magnetic drive signal from the signal processor which is representative of sound detected by the sensing microphone. The other implant main lobe is a ring magnet arrangement that is fixed to the skull bone to magnetically couple the magnetic drive signal to the skull bone which delivers the signal to the cochlea by bone conduction where it is sensed as sound by the patient.

Figure 1:
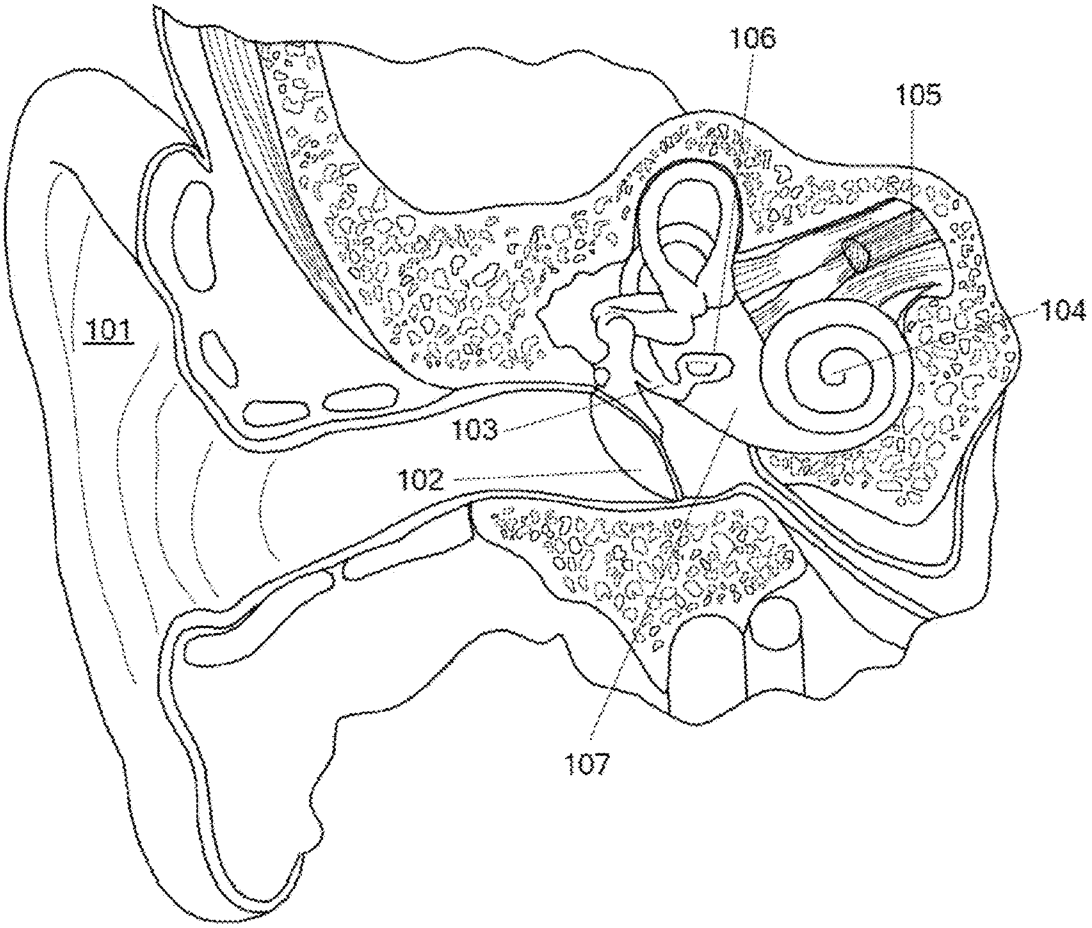
FIG. 1 shows anatomical structures of a typical human ear.
Figure 2:
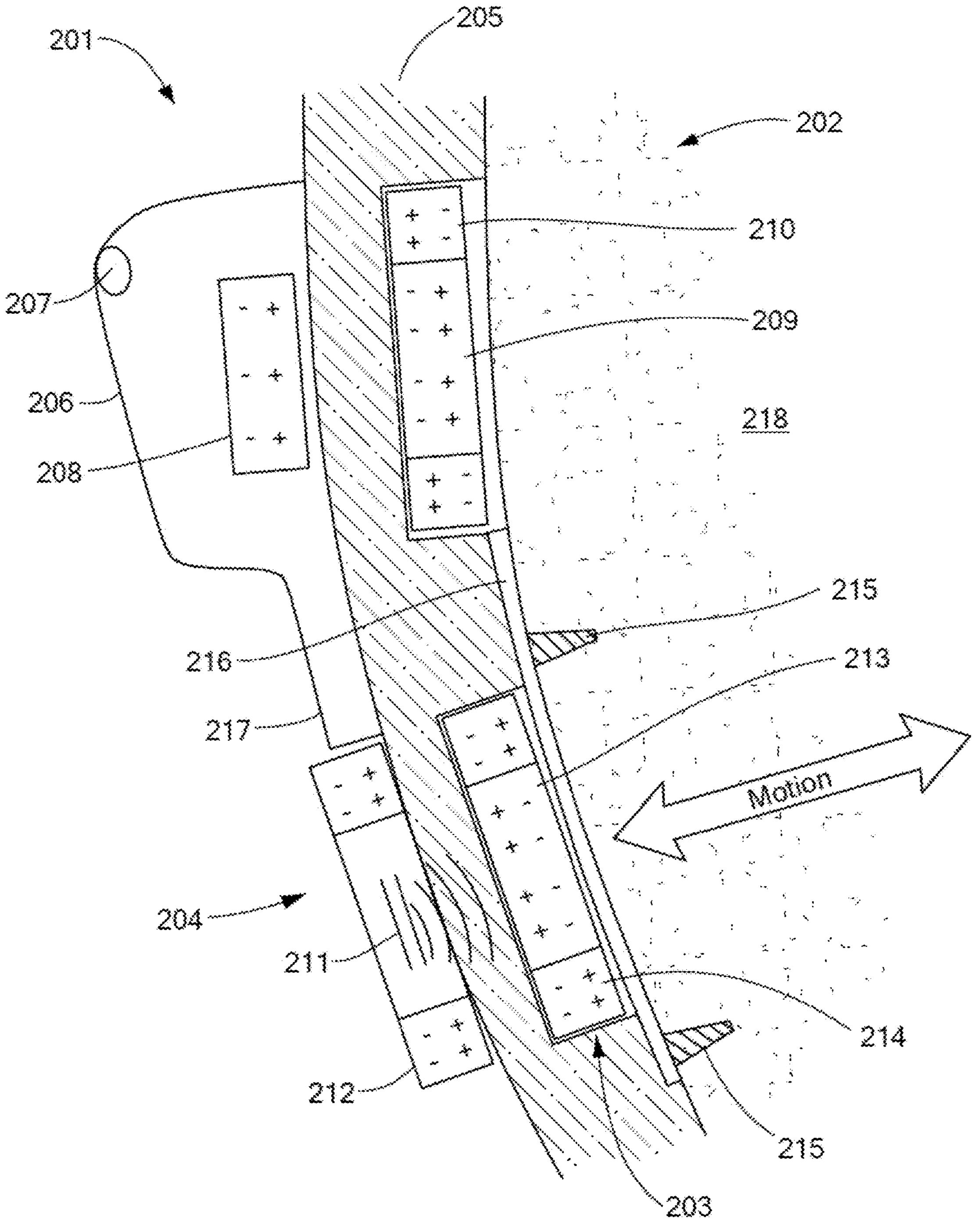
FIG. 2 shows a cross-sectional view of an implantable hearing prosthesis arrangement according to an embodiment of the present invention.

FIG. 2 shows a cross-sectional view of one exemplary embodiment of the present invention including an implantable attachment magnet 202 which is fixable beneath the skin 205 of the patient to underlying skull bone 218. The implantable attachment magnet 202 magnetically connects with a corresponding external attachment magnet 208 over the skin 205. An implantable signal transducer 203 magnetically cooperates with corresponding external signal drive coil 204 that provides an externally generated magnetic audio signal to couple a corresponding mechanical stimulation signal to the skull bone 218 for delivery by bone conduction as an audio signal to the cochlea. An implant connector member 216 flexibly connects and positions the attachment magnet 202 a fixed distance from the signal transducer 203. A corresponding external component 201 includes an external attachment magnet 208 that is fixable on the skin 205 to magnetically connect with the implant attachment magnet 202 beneath the skin 205. An external signal drive coil 204 provides the magnetic audio signal to the implant signal transducer 203 beneath the skin 205. An external connector member 217 flexibly connects and positions the external attachment magnet 208 a fixed distance from the signal drive coil 204.

In the embodiment shown in FIG. 2, the implant attachment magnet 202 is specifically implemented as an outer ring magnet 210 having a first magnetization direction and inner core magnet 209 having an opposite second magnetization direction. Likewise, the signal transducer 203 also includes an outer ring magnet 214 having a first magnetization direction and inner core magnet 213 having an opposite second magnetization direction. Such ring magnet arrangements minimize problems that can arise from strong external magnetic fields such as with magnetic resonance imaging. This subject is explored more fully in U.S. Provisional Patent Application 61/227,632, filed Jul. 22, 2009; which is incorporated herein by reference. In the embodiment shown in FIG. 2, the external attachment magnet 208 is a typical disk-shaped magnet sized adapted to magnetically connect with the inner core magnet 209 of the implant attachment magnet 202. In other embodiments, the external attachment magnet 208 may be like the implant attachment magnet 202 in having an inner core magnet that is surrounded by an outer ring magnet, both of which are sized and adapted to optimize the magnetic connection with the implant attachment magnet 202. Similarly, the external signal drive coil 204 shown in the embodiment in FIG. 2 includes an outer ring magnet 212 sized and magnetically adapted to optimize the cooperation with the outer ring magnet 214 of the implanted signal transducer 203. The inner core 211 of the signal drive coil 204 includes an electromagnetic coil (with or without a core) that produces the magnetic audio signal which is coupled across the skin to the implanted signal transducer 203.

Figure 3B:
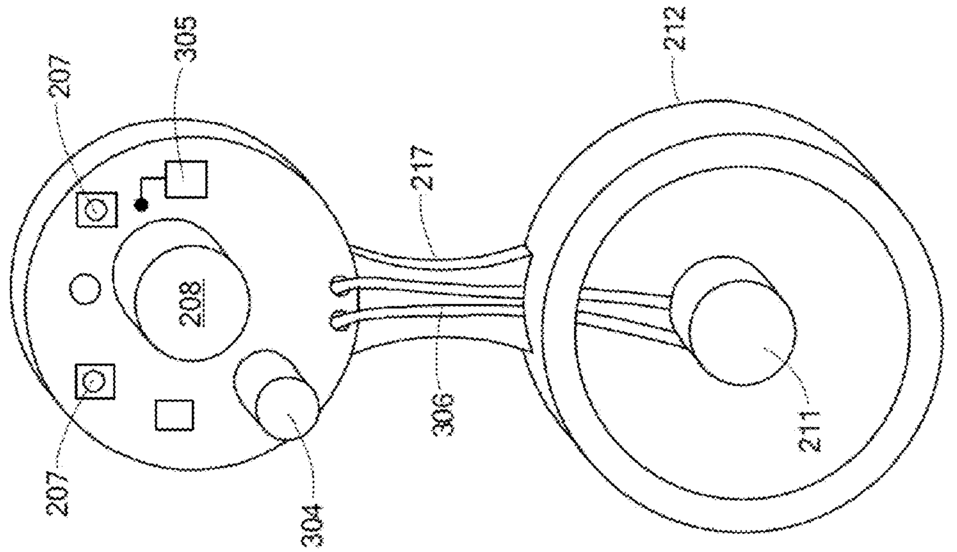
FIG. 3 A-B shows top plan views of the outside and internal structures of an external component for an embodiment of the invention.
Figure 3A:
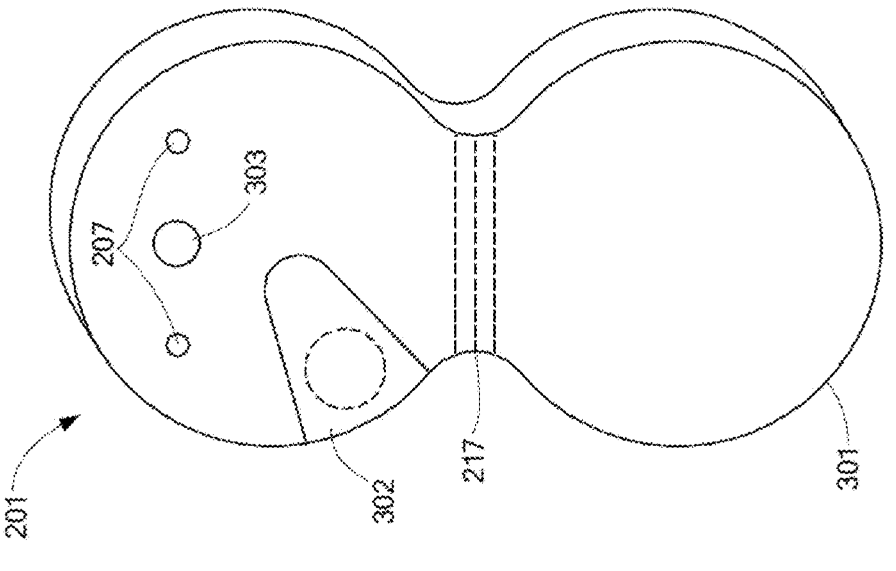

FIG. 3 A-B shows top plan views providing further detail regarding the outside and internal structures of the external component 201. The external attachment magnet 208 is contained within a processor housing 301 made of an impact resistant material such as plastic. A battery compartment 302 contains a battery power supply 304 that provides electrical power to the external component 201. The processor housing 301 also contains openings for one or more sensing microphones 207 that sense the nearby acoustic environment and generate a representative microphone signal output. A signal processor 305 within the processor housing 301 receives the microphone signal and generates a corresponding electrical stimulation signal output. Signal leads 303 in the flexible member 217 couple the electrical stimulation signal from the signal processor 305 to the signal drive coil 204 for output to the implant.

Figure 4:
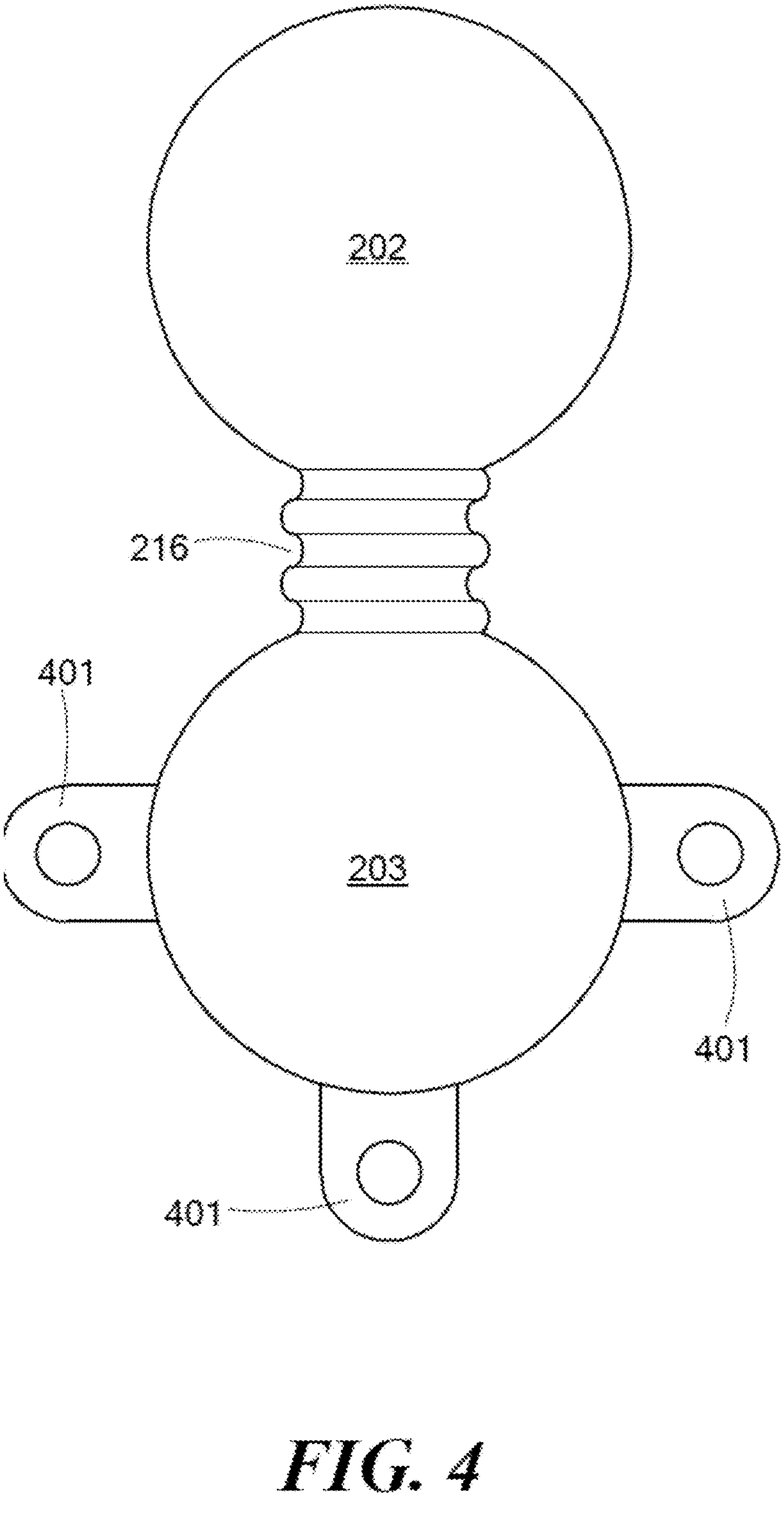
FIG. 4 shows a top plan view of the implant portion of an embodiment of the invention.

FIG. 4 shows a top plan view providing further detail regarding the implant portion used in FIG. 2. The implant signal transducer 203 may be adapted for fixed attachment to the skull bone 218 by one or more bone screws 215 through corresponding flange openings 401 distributed around the outer circumference of the implant signal transducer 203. Alternatively or in addition, some embodiments may be adapted for fixation of the signal transducer 203 in a prepared recessed transducer well in the skull bone 218. The lobe of the signal transducer 203 and/or the lobe of the implant attachment magnet 202 may be hermetically enclosed such as with a biocompatible membrane.

Figure 5:
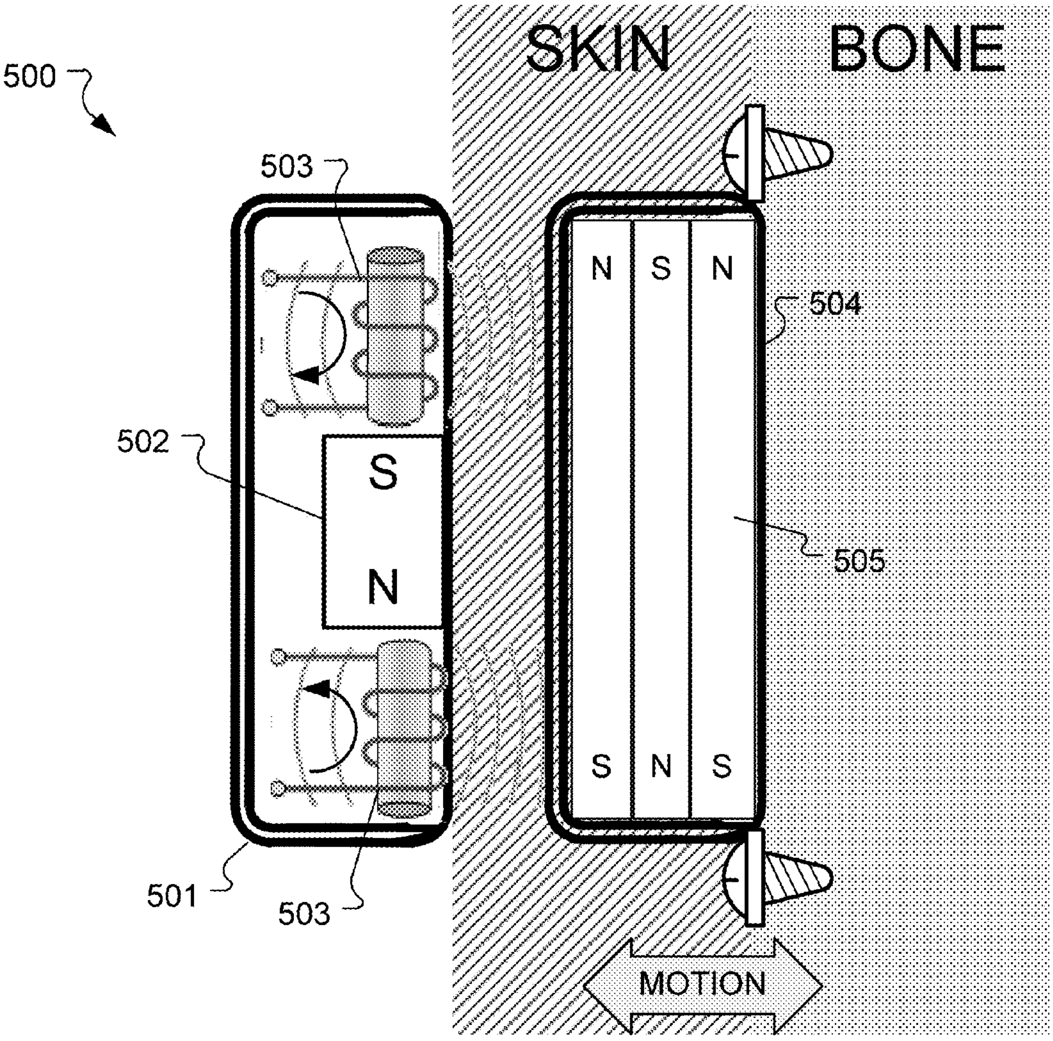
FIG. 5 shows various aspects of an external component according to another embodiment of the present invention.

While the specific embodiment depicted in FIG. 2 shows an external component with a signal drive arrangement based on an electromagnetic drive coil surrounded by a ring permanent magnet, the invention is not necessarily limited to such a specific structure. For example, FIG. 5 shows various aspects of an external component 500 according to another embodiment of the present invention. An external housing 501 contains an attachment magnet 502 configured to magnetically connect with one or more implant magnets 505 in an implanted signal transducer 504. A pair of external electromagnetic drive coils 503 are located within the external housing 501 adjacent to the attachment magnet 502 configured such that their respective magnetic drive signals have opposing magnetic directions. The drive coils 503 conduct electrical current to develop magnetic drive signals through the skin to the implanted signal transducer 504 to generate responsive vibrations of the signal transducer 504 for perception by the patient as sound.

The external attachment magnet 502 cooperates most strongly with the closest counterpart implant magnet 505 within the implanted signal transducer 504. In the specific embodiment in FIG. 5, the implanted signal transducer 504 is shown having a stack of three implant magnets 505 with alternating different lateral magnetization directions. This arrangement improves the compatibility of the implanted signal transducer 504 with the far field of MRI imaging systems—the sum of the magnetic moments of the implant magnets 504 with a N/S magnetization direction should be substantially equal to the sum of the magnetic moments of the magnets with S/N magnetization direction. And different embodiments may have different numbers and specific arrangements of the implant magnet 505, and so instead of three magnets (as shown), there may be one, two, four or more with their own specific magnetic orientation arrangements.

The external housing 501 can contain other components such as a signal processor for generating electrical drive signals for the electromagnetic drive coils 503. There also may be a sensing microphone for developing an audio input signal to the signal processor. Alternatively, an embodiment may be arranged more like in FIG. 2 with a separate attached housing that encloses other components such as a signal processor, microphone, power supply, etc.

One advantage embodiments of the present invention possess which is lacking in earlier arrangements such as FMT-based systems is that there is no requirement that the implanted components include electronic circuits and associated power circuitry. The prior art has to convert a received electrical signal and therefore must have some necessary functional overhead including electrical power and signal conversion circuitry. But with embodiments of the present invention there is simply no requirement for any subcutaneous electronic circuitry.

Embodiments of the present invention such as those described above can be easily and directly implemented in existing products with corresponding size and geometry replacement magnets, either for the implanted magnet and/or the external magnet. Embodiments may usefully contain permanent magnetic material and/or ferro-magnetic material as well as other structural materials. These include without limitation magnetic ferrite materials such as $Fe_3O_4$, $BaFe_{12}O_{19}$ etc., compound materials such as plastic bonded permanent magnetic powder, and/or sintered material such as sintered NdFeB, SmCo, etc. Selection of the proper materials and arrangements may help avoid or reduce undesired eddy currents.

Although various exemplary embodiments of the invention have been disclosed, it should be apparent to those skilled in the art that various changes and modifications can be made which will achieve some of the advantages of the invention without departing from the true scope of the invention.

What is claimed is:

1. An external component for a hearing implant, the component comprising:

an external housing containing an attachment magnet configured to magnetically connect with an implant magnet of an implanted signal transducer;

a pair of external electromagnetic drive coils within the external housing adjacent to the attachment magnet for conducting electrical current to develop magnetic drive signals through the skin to the signal transducer to generate responsive vibrations of the signal transducer for perception by the patient as sound;

wherein the drive coils are configured such that their respective magnetic drive signals have opposing magnetic directions.

2. An external component according to claim 1, further comprising:

a signal processor for generating electrical drive signals for the electromagnetic drive coils.

3. An external component according to claim 2, wherein the signal processor is enclosed within the external housing.

4. An external component according to claim 2, wherein the signal processor is enclosed within a signal processor housing separate from and connected to the external housing.

5. An external component according to claim 2, further comprising:

at least one sensing microphone for developing an audio input signal to the signal processor.

* * * * *